United States Patent
Capanema et al.

(10) Patent No.: US 10,233,281 B2
(45) Date of Patent: Mar. 19, 2019

(54) METHODS FOR PREPARING AND COLLECTING POLYAROMATIC COMPOUNDS, AND PRODUCTS COMPRISING POLYAROMATIC COMPOUNDS

(71) Applicant: RENMATIX, INC., King of Prussia, PA (US)

(72) Inventors: Ewellyn A. Capanema, Wayne, PA (US); Mikhail Y. Balakshin, Wayne, PA (US); Matyas Kosa, Vancouver (CA); Stephen Herbert Harris, Kennett Square, PA (US)

(73) Assignee: Renmatix, Inc., King of Prussia, PA (US)

( * ) Notice: Subject to any disclaimer, the term of this patent is extended or adjusted under 35 U.S.C. 154(b) by 3 days.

(21) Appl. No.: 15/511,071

(22) PCT Filed: Sep. 25, 2015

(86) PCT No.: PCT/US2015/052422
§ 371 (c)(1),
(2) Date: Mar. 14, 2017

(87) PCT Pub. No.: WO2016/049564
PCT Pub. Date: Mar. 31, 2016

(65) Prior Publication Data
US 2017/0275417 A1    Sep. 28, 2017

Related U.S. Application Data

(60) Provisional application No. 62/056,072, filed on Sep. 26, 2014, provisional application No. 62/166,841, filed on May 27, 2015.

(51) Int. Cl.
*C08G 61/10* (2006.01)
*C08G 8/00* (2006.01)
(Continued)

(52) U.S. Cl.
CPC .............. *C08G 61/10* (2013.01); *C01B 17/69* (2013.01); *C08G 8/00* (2013.01); *C08G 61/125* (2013.01);
(Continued)

(58) Field of Classification Search
CPC ...................................................... C08G 61/10
(Continued)

(56) References Cited

U.S. PATENT DOCUMENTS

| 5,597,714 A | 1/1997 | Farone et al. |
| 8,759,498 B2 | 6/2014 | Kilambi et al. |

(Continued)

FOREIGN PATENT DOCUMENTS

| WO | WO-2011/091044 A1 | 7/2011 |
| WO | WO-2012/151509 A2 | 11/2012 |

(Continued)

OTHER PUBLICATIONS

Adler, E. et al., Investigation of the Acid-Catalysed Alkylation of Lignins by Means of NMR Spectroscopic Methods. Holzforschung. 1987; 41(4):199-207.
(Continued)

*Primary Examiner* — Duc Truong
(74) *Attorney, Agent, or Firm* — Ballard Spahr LLP

(57) ABSTRACT

Disclosed are methods for preparing and collecting a polyaromatic compound. Also disclosed are products comprising a polyaromatic compound.

20 Claims, 2 Drawing Sheets

(51) Int. Cl.

| | |
|---|---|
| *C08L 97/00* | (2006.01) |
| *C08H 8/00* | (2010.01) |
| *C08G 61/12* | (2006.01) |
| *C01B 17/69* | (2006.01) |
| *C08H 7/00* | (2011.01) |
| *C09J 161/06* | (2006.01) |
| *C09J 197/00* | (2006.01) |
| *C12N 9/14* | (2006.01) |
| *C08G 8/10* | (2006.01) |

(52) U.S. Cl.
CPC ............. *C08G 61/126* (2013.01); *C08H 6/00* (2013.01); *C08H 8/00* (2013.01); *C08L 97/00* (2013.01); *C09J 161/06* (2013.01); *C09J 197/005* (2013.01); *C08G 8/10* (2013.01); *C08G 2261/312* (2013.01); *C08G 2261/3222* (2013.01); *C08G 2261/3223* (2013.01); *C12N 9/14* (2013.01); *Y02P 20/145* (2015.11)

(58) Field of Classification Search
USPC ........................................................ 528/86
See application file for complete search history.

(56) References Cited

U.S. PATENT DOCUMENTS

| | | |
|---|---|---|
| 9,255,188 B2 | 2/2016 | Kilambi et al. |
| 2011/0124057 A1 | 5/2011 | Genta et al. |
| 2012/0282465 A1 | 11/2012 | Kadam et al. |
| 2012/0282466 A1 | 11/2012 | Iyer et al. |
| 2012/0282467 A1 | 11/2012 | Iyer et al. |
| 2012/0291774 A1 | 11/2012 | Kilambi et al. |
| 2013/0172540 A1 | 7/2013 | Simard et al. |
| 2013/0239954 A1 | 9/2013 | Kilambi et al. |
| 2014/0014092 A1 | 1/2014 | Kazachkin et al. |
| 2014/0030524 A1 | 1/2014 | Kadam et al. |
| 2014/0039144 A1 | 2/2014 | Simard et al. |
| 2014/0275501 A1 | 9/2014 | Capanema et al. |
| 2015/0176091 A1 | 6/2015 | Kazachkin et al. |
| 2016/0108182 A1 | 4/2016 | Kilambi et al. |
| 2016/0244852 A1 | 8/2016 | Kilambi et al. |

FOREIGN PATENT DOCUMENTS

| | | |
|---|---|---|
| WO | WO-2012/151524 A2 | 11/2012 |
| WO | WO-2012/151526 A2 | 11/2012 |
| WO | WO-2013070160 A1 | 5/2013 |
| WO | WO-2013/101397 A1 | 7/2013 |
| WO | WO-2014/012030 A1 | 1/2014 |
| WO | WO-2014/144746 A1 | 9/2014 |
| WO | WO-2016/049564 A1 | 3/2016 |
| WO | WO-2016/049567 A1 | 3/2016 |
| WO | WO-2016/049569 A1 | 3/2016 |
| WO | WO-2016/144287 A1 | 9/2016 |

OTHER PUBLICATIONS

Capanema, E.A. et al. (2005) Isolation and Characterization of Residual Lignins from Hardwood Pulps: Method Improvements. Proc. 13th Intern. Symp. Wood Fibre Pulping C., Auckland, New Zealand, v.III, 57-64.

Sluiter, A. et al., Nrel Technical Report NREL/TP-510-42618, Determination of Structural Carbohydrates and Lignin in Biomass. Laboratory Analytical Procedure. Natl Renewable Energy Laboratory. Issued—2008; Revised—2012 (18 pages).

International Search Report and Written Opinion dated Jan. 6, 2016 by the International Searching Authority for Patent Application No. PCT/US2015/052422, which was filed on Sep. 25, 2015 and published as WO 2016/049564 on Mar. 31, 2016 (Inventor—Capanema et al.; Applicant—Renmatix, Inc.) (9 pages).

International Preliminary Report on Patentability dated Mar. 28, 2017 by the International Searching Authority for Patent Application No. PCT/US2015/052422, which was filed on Sep. 25, 2015 and published as WO 2016/049564 on Mar. 31, 2016 (Inventor—Capanema et al.; Applicant—Renmatix, Inc.) (6 pages).

European Search Report dated Apr. 19, 2018 by the European Patent office for EP Application No. 15844967.8, filed Sep. 25, 2015, and published as EP 3186296 on Jul. 5, 2017 (Applicant—Renmatix Inc.) (6 pages).

METHODS FOR PREPARING AND COLLECTING POLYAROMATIC COMPOUNDS, AND PRODUCTS COMPRISING POLYAROMATIC COMPOUNDS

CROSS-REFERENCE TO RELATED APPLICATIONS

This application claims the benefit of U.S. Application No. 62/056,072 filed Sep. 26, 2014, and U.S. Application No. 62/166,841 filed May 27, 2015, the entire disclosures of which are incorporated herein by reference.

FIELD OF THE INVENTION

The invention generally relates to methods for preparing and collecting a polyaromatic compound. The invention also generally relates to products comprising a polyaromatic compound.

BRIEF SUMMARY OF THE INVENTION

In some embodiments, provided is a method comprising: a first subjecting step, wherein a first biomass is subjected to a first fluid comprising hot compressed water, thereby forming a first mixture; wherein the first mixture comprises a first liquid fraction comprising a first solubilized polyaromatic compound; a first acidifying step, wherein a first liquid comprising the first solubilized polyaromatic compound is acidified at a temperature of at least about 90° C., thereby forming a second mixture comprising a first precipitated polyaromatic compound; and a first collecting step, wherein at least a portion of the first precipitated polyaromatic compound is collected, thereby obtaining a first collected precipitated polyaromatic compound; wherein a substantial portion of the first collected precipitated polyaromatic compound is not discarded.

In some embodiments, the first mixture further comprises a first solid fraction, and at least a portion of the first solid fraction or a first solid derived from the first solid fraction is, in a second subjecting step, subjected to a third fluid comprising hot compressed water, thereby forming a third mixture, wherein the third mixture comprises a second liquid fraction comprising a second solubilized polyaromatic compound.

In some embodiments, provided herein is a second acidifying step, wherein a second liquid comprising the second solubilized polyaromatic compound is acidified at a temperature of at least about 90° C., thereby forming a fourth mixture comprising a second precipitated polyaromatic compound; and a second collecting step, wherein at least a portion of the second precipitated polyaromatic compound is collected, thereby obtaining a second collected precipitated polyaromatic compound; wherein a substantial portion of the second collected precipitated polyaromatic compound is not discarded.

In some embodiments, provided herein is a product capable of sale, barter, trade, or any combination thereof comprising a polyaromatic compound, wherein, prior to incorporation of the polyaromatic compound into the product, the polyaromatic compound has: a total carbonyl content of at least about 36 units, per 100 aromatic units.

In some embodiments, provided herein is a product capable of sale, barter, trade, or any combination thereof comprising a polyaromatic compound, wherein, prior to incorporation of the polyaromatic compound into the product, the polyaromatic compound has: a non-conjugated carbonyl content of at least about 17 units, per 100 aromatic units.

In some embodiments, provided herein is a product capable of sale, barter, trade, or any combination thereof comprising a polyaromatic compound, wherein, prior to incorporation of the polyaromatic compound into the product, the polyaromatic compound has: conjugated carbonyl content of at least about 12 units, per 100 aromatic units.

In some embodiments, provided herein is a product capable of sale, barter, trade, or any combination thereof comprising a polyaromatic compound, wherein, prior to incorporation of the polyaromatic compound into the product, the polyaromatic compound has: a methoxyl content of less than about 110 units, per 100 aromatic units.

BRIEF DESCRIPTION OF THE DRAWINGS

The accompanying drawings, which are included to provide a further understanding of the invention and are incorporated in and constitute a part of this specification, illustrate aspects of the invention and together with the description serve to explain the principles of the invention. In the drawings.

DETAILED DESCRIPTION OF THE INVENTION

Figure 1:
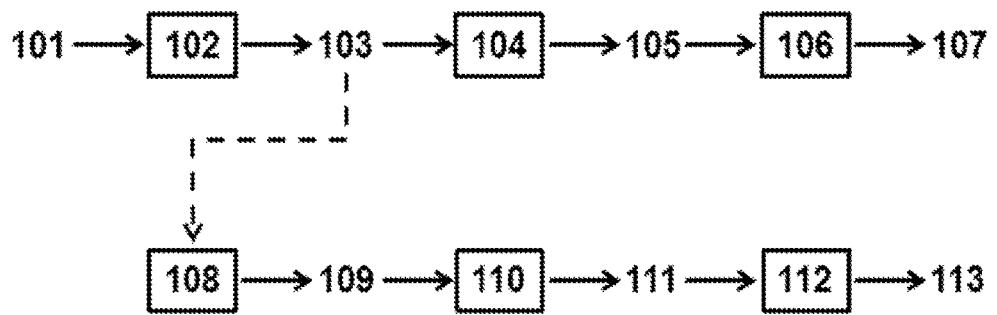
FIG. 1 illustrates a combination of several embodiments of the methods described herein.

As employed above and throughout the disclosure, the following terms, unless otherwise indicated, shall be understood to have the following meanings.

As used herein, the phrase "substantially free" means have no more than about 1%, preferably less than about 0.5%, more preferably, less than about 0.1%, by weight of a component, based on the total weight of any composition containing the component.

As used herein, the singular forms "a," "an," and "the" include the plural reference unless the context clearly indicates otherwise.

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." In this manner, slight variations from a stated value can be used to achieve substantially the same results as the stated value. Also, the disclosure of ranges is intended as a continuous range including every value between the minimum and maximum values recited as well as any ranges that can be formed by such values. Also disclosed herein are any and all ratios (and ranges of any such ratios) that can be formed by dividing a recited numeric value into any other recited numeric value.

Accordingly, the skilled person will appreciate that many such ratios, ranges, and ranges of ratios can be unambiguously derived from the numerical values presented herein and in all instances such ratios, ranges, and ranges of ratios represent various embodiments of the present invention.

A supercritical fluid is a fluid at a temperature above its critical temperature and at a pressure above its critical pressure. A supercritical fluid exists at or above its "critical point," the point of highest temperature and pressure at which the liquid and vapor (gas) phases can exist in equilibrium with one another. Above critical pressure and critical temperature, the distinction between liquid and gas phases disappears. A supercritical fluid possesses approximately the penetration properties of a gas simultaneously with the solvent properties of a liquid. Accordingly, supercritical fluid extraction has the benefit of high penetrability and good solvation.

Reported critical temperatures and pressures include: for pure water, a critical temperature of about 374.2° C., and a critical pressure of about 221 bar; for carbon dioxide, a critical temperature of about 31° C. and a critical pressure of about 72.9 atmospheres (about 1072 psig). Near critical water has a temperature at or above about 300° C. and below the critical temperature of water (374.2° C.), and a pressure high enough to ensure that all fluid is in the liquid phase. Sub-critical water has a temperature of less than about 300° C. and a pressure high enough to ensure that all fluid is in the liquid phase. Sub-critical water temperature may be greater than about 250° C. and less than about 300° C., and in many instances sub-critical water has a temperature between about 250° C. and about 280° C.

As used herein, "hot compressed water" ("HCW") is water that is at a temperature at or above 100° C. and at a pressure above atmospheric pressure, such that some or all of the water is present in liquid or supercritical form. In some embodiments, the pressure is sufficient to ensure that all of the water is present in liquid or supercritical form (i.e., water is not present in vapor form). In some embodiments, HCW is subcritical water. In some embodiments, HCW is near-critical water. In some embodiments, HCW is supercritical water. As used herein, "a fluid comprising hot compressed water" indicates that the fluid comprises water, and the fluid is at a temperature at or above 100° C. and at a pressure above atmospheric pressure.

Biomass is a renewable energy source generally comprising carbon-based biological material derived from recently-living organisms. The organisms may have been plants, animals, fungi, etc. Examples of biomass include without limitation wood, lignocellulosic biomass, cellulose (e.g., microcrystalline cellulose, nanocrystalline cellulose, cotton, etc.), municipal solid waste, manufacturing waste (wood residues such as sawmill and paper mill discards), agricultural residues (including corn stover, sugarcane bagasse, rice hulls, oat hulls, etc.), food waste, etc. Wood can be, for example, hardwood, softwood, annual fibers, and combinations thereof. Biomass typically comprises cellulose, hemicellulose, and lignin. Fossil fuels are generally not considered biomass even though ultimately derived from carbon-based biological material. The term "biomass" as used herein does not include fossil fuel sources. Lignocellulosic biomass, as used herein, includes any material that comprises lignin and cellulose, such as substantially unprocessed wood, as well as residues resulting from processing wood. As used herein, "raw biomass" or "raw lignocellulosic biomass" means biomass that has not been subjected, or has not been substantially subjected, to a hydrolysis process, an extraction process, and/or chemical treatment. Comminuted (e.g., ground or milled) biomass is considered to be "raw biomass." "Has not been substantially subjected" means that raw lignocellulosic biomass may have been fleetingly subjected to one of the indicated processes/treatments (intentionally or unintentionally), but the composition and molecular structure (e.g., hemicellulose, cellulose, and lignin content) of the raw lignocellulosic biomass is still substantially similar to the raw lignocellulosic biomass before such fleeting processes/treatments. For example, if a hardwood raw lignocellulosic biomass in the form of woodchips is subjected to a temperature of about 90° C. for about 10 minutes or less (e.g., as a washing step to remove impurities, dirt, debris, etc.), these conditions would not substantially change the composition of the raw lignocellulosic biomass, such that the raw lignocellulosic biomass has not been substantially subjected to a process/treatment, as defined herein.

As used herein, a "polyaromatic compound" is a compound (e.g., polymer or oligomer) that contains more than one aromatic moiety, such as a benzene ring, a furan ring, a thiophene ring, and the like, which rings can be substituted or unsubstituted. Example polyaromatic compounds include, for example, lignin, polyfuran, pseudolignin, and the like.

As used herein, "pseudolignin" means a compound that is polyaromatic in nature (e.g., polymer or oligomer containing more than one aromatic moiety), and which contributes to the acid insoluble lignin content as measured according to NREL/TP-510-42618 (Sluiter A., et al.; NREL Technical Report, "Determination of Structural Carbohydrates and Lignin in Biomass," Laboratory Analytical Procedure, Issued April 2008, Revised August 2012.), but that is not generally considered to be "lignin" by those of ordinary skill in the art.

As used herein, "discarding" means disposing of a material in a manner such that little or no economic remuneration is gained from disposing of the material. An example of discarding a material is providing the material to a trash or hazardous waste collection company for disposal in a landfill or other suitable repository. Another example of discarding a material is providing the material to a third party free of charge or for insignificant remuneration. In some embodiments, combustion of a material is considered to be discarding of the material, even if, e.g., such combusting provides heating value that can offset some heating requirements of, e.g., an industrial, residential, or commercial process. In some embodiments, selling a material, bartering a material, trading a material, or any combination thereof, is not considered to be discarding the material.

The terms "subjecting," "acidifying," and "collecting" are consistently used herein to designate particular types of steps in the methods disclosed herein. For example, the "subjecting" step is designated as being a "first," "second," "third," etc., subjecting step, simply to differentiate subjecting steps in embodiments where more than one subjecting step may be (but is not necessarily) performed. Even though each specific subjecting step is independent and can be the same or different from any other subjecting step, each subjecting step (e.g., "first," "second," etc.) typically falls within a general range of conditions (e.g., temperature, pressure, residence time, etc.). As such, the subjecting step is described herein in general terms, but the ranges for the conditions of each of the "first," "second," "third," "fourth," etc., subjecting steps can be independently selected from the ranges of conditions generally described herein for the "subjecting step." The same applies to the "acidifying" and "collecting" steps.

In some embodiments, provided herein is a method comprising: a first subjecting step, wherein a first biomass is subjected to a first fluid comprising hot compressed water, thereby forming a first mixture; wherein the first mixture comprises a first liquid fraction comprising a first solubilized polyaromatic compound; a first acidifying step, wherein a first liquid comprising the first solubilized polyaromatic compound is acidified at a temperature of at least about 90° C., thereby forming a second mixture comprising a first precipitated polyaromatic compound; and a first collecting step, wherein at least a portion of the first precipitated polyaromatic compound is collected, thereby obtaining a first collected precipitated polyaromatic compound; wherein a substantial portion of the first collected precipitated polyaromatic compound is not discarded. In some embodiments, the first liquid fraction, first liquid, or both, comprises C5 saccharides (e.g., hemicellulose, xylose, xylose oligomers, etc.), C6 saccharides (glucose, glucose oligomers, mannose, mannose oligomers, etc.), or a combination thereof.

In some embodiments, the first mixture further comprises a first solid fraction, and at least a portion of the first solid fraction or a first solid derived from the first solid fraction is, in a second subjecting step, subjected to a third fluid comprising hot compressed water, thereby forming a third mixture, wherein the third mixture comprises a second liquid fraction comprising a second solubilized polyaromatic compound. In some embodiments, the first solid fraction comprises cellulose, lignin, or a combination thereof. In some embodiments, the second liquid fraction comprises C6 saccharides (glucose, glucose oligomers, mannose, mannose oligomers, or any combination thereof).

In some embodiments, the methods described herein employ a second acidifying step, wherein a second liquid comprising the second solubilized polyaromatic compound is acidified at a temperature of at least about 90° C., thereby forming a fourth mixture comprising a second precipitated polyaromatic compound; and a second collecting step, wherein at least a portion of the second precipitated polyaromatic compound is collected, thereby obtaining a second collected precipitated polyaromatic compound; wherein a substantial portion of the second collected precipitated polyaromatic compound is not discarded. In some embodiments, the second liquid comprises C6 saccharides (glucose, glucose oligomers, mannose, mannose oligomers, or any combination thereof).

The first biomass employed in the first subjecting step can be any suitable biomass. In some embodiments, the first biomass is raw biomass, as defined herein. In some embodiments, the first biomass is lignocellulosic biomass. In some embodiments, the first biomass is obtained by a process selected from the group consisting of acid hydrolysis, enzymatic hydrolysis, sulfur dioxide treatment, hot compressed water treatment, and any combination thereof. In some embodiments, the first biomass is in the form of chips (e.g., 1/8", 2/8", 3/8", 4/8", 5/8", 6/8", or 7/8" chips—each of the foregoing numbers can be preceded by the word "about," "at least about," or "less than about," and any of the foregoing numbers can be used singly to describe an open-ended range or in combination to describe a close-ended range). In some embodiments, the first biomass is the form of particles (e.g., having an average particle size of 500 µm, 400 µm, 300 µm, 200 µm, 100 µm, or 50 µm—each of the foregoing numbers can be preceded by the word "about," "at least about," or "less than about," and any of the foregoing numbers can be used singly to describe an open-ended range or in combination to describe a close-ended range).

The subjecting step(s) of the methods described herein comprises the use of a fluid. The fluid can have any suitable temperature and pressure. While the fluid may have various numeric designations herein (e.g., first, third, etc.), the fluid(s) used in any subjecting step falls within a general range. The conditions described herein for the fluid in a subjecting step can be used to independently define the conditions for the fluid in any subjecting step (e.g., the first, second, third, fourth, fifth, sixth, etc., subjecting step). The conditions of the fluid in each subjecting step may be the same or different from one another (i.e., they are independent).

The fluid (e.g., first fluid, third fluid, etc.) in any subjecting step can have any suitable temperature, e.g., a temperature of 100° C., 105° C., 110° C., 115° C., 120° C., 125° C., 130° C., 135° C., 140° C., 145° C., 150° C., 155° C., 160° C., 165° C., 170° C., 175° C., 180° C., 185° C., 190° C., 195° C., 200° C., 210° C., 220° C., 230° C., 240° C., 250° C., 260° C., 270° C., 280° C., 290° C., 300° C., 310° C., 320° C., 330° C., 340° C., 350° C., 360° C., 370° C., 374° C., 380° C., 390° C., 400° C., 410° C., 420° C., 430° C., 440° C., 450° C., 460° C., 470° C., 480° C., 490° C., 500° C., 510° C., 520° C., 530° C., 540° C., 550° C., 560° C., 570° C., 580° C., 590° C., or 600° C. Each of the foregoing numbers can be preceded by the word "about," "at least about," or "less than about," and any of the foregoing numbers can be used singly to describe an open-ended range or in combination to describe a close-ended range. In some embodiments, the fluid (e.g., first fluid, third fluid, etc.) in any subjecting step (e.g., first subjecting step, second subjecting step, etc.) has a temperature of about 130° C. to about 374° C. In some embodiments, the fluid (e.g., first fluid, third fluid, etc.) in any subjecting step (e.g., first subjecting step, second subjecting step, etc.) comprises supercritical water (i.e., the fluid comprises hot compressed water, and the hot compressed water in the fluid is supercritical water).

The fluid (e.g., first fluid, third fluid, etc.) in any subjecting step can have any suitable pressure above atmospheric pressure, e.g., 2 bar, 5 bar, 10 bar, 15 bar, 20 bar, 25 bar, 30 bar, 35 bar, 40 bar, 45 bar, 50 bar, 55 bar, 60 bar, 65 bar, 70 bar, 75 bar, 80 bar, 85 bar, 90 bar, 95 bar, 100 bar, 110 bar, 120 bar, 130 bar, 140 bar, 150 bar, 160 bar, 170 bar, 180 bar, 190 bar, 200 bar, 210 bar, 220 bar, 221, bar, 230 bar, 240 bar, 250 bar, 260 bar, 270 bar, 280 bar, 290 bar, 300 bar, 310 bar, 320 bar, 330 bar, 340 bar, 350 bar, 360 bar, 370 bar, 380 bar, 390 bar, 400 bar, 410 bar, 420 bar, 430 bar, 440 bar, 450 bar, 460 bar, 470 bar, 480 bar, 490 bar, or 500 bar. Each of the foregoing numbers can be preceded by the word "about," "at least about," or "less than about," and any of the foregoing numbers can be used singly to describe an open-ended range or in combination to describe a close-ended range.

The residence time of any subjecting step (i.e., the time period that a specified feedstock is subjected to a particular temperature and pressure) can be any suitable residence time. Typical residence times of the subjecting step are 0.01 sec, 0.05 sec, 0.1 sec, 0.2 sec, 0.3 sec, 0.4 sec, 0.5 sec, 0.6 sec, 0.7 sec, 0.8 sec, 0.9 sec, 1 sec, 1.5 sec, 2 sec, 2.5 sec, 3 sec, 4 sec, 5 sec, 6 sec, 7 sec, 8 sec, 9 sec, 10 sec, 20 sec, 30 sec, 40 sec, 50 sec, 60 sec, 90 sec, 2 min, 2.5 min, 3 min, 4 min, 5 min, 10 min, 15 min, 20 min, 30 min, 40 min, 50 min, 60 min, 70 min, 80 min, 90 min, 2 hrs, 2.5 hrs, 3 hrs, 3.5 hrs, 4 hrs, 4.5 hrs, 5 hrs, 5.5 hrs, 6 hrs, 6.5 hrs, 7 hrs, 7.5 hrs, 8 hrs, 8.5 hrs, or 9 hrs. Each of the foregoing numbers can be preceded by the word "about," "at least about," or "less than about," and any of the foregoing numbers can be used singly to describe an open-ended range or in combination to describe a close-ended range.

Residence time is inversely proportional to temperature. In other words, as the temperature increases, the residence time decreases. Generally, non-limiting approximate examples of pairings of temperatures and residence times include about 0.01 to about 10 sec for temperatures of about 300° C. to about 550° C.; about 30 sec to 5 min for temperatures of about 200° C. to about 300° C., and about 10 min to about 3 hours for temperatures of about 130° C. to about 200° C. However, any of the temperatures and residence times can be paired together to describe the conditions of the subjecting step.

The fluid in any subjecting step can be any suitable fluid. For example, the fluid (e.g., first fluid, third fluid, etc.) can comprise, consist of, or consist essentially of hot compressed water. In some embodiments, the fluid in any subjecting step can comprise methanol, ethanol, propanol, butanol, or any combination thereof. In some embodiments, the fluid in any subjecting step comprises an acid (e.g., sulfuric acid, hydrochloric acid, phosphoric acid, nitric acid, added or recycled acetic acid, or any combination thereof). In some embodiments, the fluid (e.g., first fluid, third fluid, etc.) in any subjecting step (e.g., first subjecting step, second subjecting step, etc.) is substantially free of added acid. As used herein, "added acid" means any acid that is not internally produced during the subjecting step (such as internally produced acetic acid due to cleavage of acetate groups on the biomass itself). As used herein, acetic acid that is produced from biomass hydrolysis during one hydrolysis reaction that is recycled back to a different hydrolysis reaction is considered added acid. Any of the descriptions of fluid options can be combined in any manner to describe the fluid used in any subjecting step.

The first subjecting step subjects a first biomass to a first fluid comprising hot compressed water, thereby forming a first mixture. The first mixture comprises a first liquid fraction comprising a first solubilized polyaromatic compound. As used herein, "solubilized" means that at least a portion of the polyaromatic compound is dissolved in solution (e.g., at least about 30 wt. %, 40 wt. %, 50 wt. %, 60 wt. %, 70 wt. %, 80 wt. %, 90 wt. %, 95 wt. %, or 99 wt. % of the polyaromatic compound is dissolved in solution, based on the total weight of the polyaromatic compound). In some embodiments, the first mixture further comprises a first solid fraction. In some embodiments, the first liquid fraction can remain part of the first mixture (which can include a first solid fraction) when the first liquid fraction is acidified in the first acidifying step (i.e., the first liquid fraction is not separated from the first solid fraction, if present, prior to the acidifying step). In some embodiments, the first mixture further comprises a first solid fraction, and the method further comprises separating at least a portion of the first solid fraction from the first liquid fraction prior to the first acidifying step. In some embodiments, the first liquid fraction (with or without separation from the first solid fraction) is treated in some manner (e.g., concentration, chemical treatment, membrane filtration, etc.), thereby forming a first liquid comprising the first solubilized polyaromatic compound, prior to acidifying the first liquid in the first acidifying step. In this way, "first liquid" can be the same or different from the "first liquid fraction." This same type of description applies to the "second liquid" employed in the optional "second acidifying step" described elsewhere herein. Separating can be performed by any suitable method known in the art, e.g., filtering, filter press, centrifuge, decanting, cyclone separation, etc., or any combination thereof.

In some embodiments, the first mixture further comprises a first solid fraction, and at least a portion (10 wt. %, 20 wt. %, 30 wt. %, 40 wt. %, 50 wt. %, 60 wt. %, 70 wt. %, 80 wt. %, 90 wt. %, 95 wt. %, 99 wt. %, or 100 wt. %—each of the foregoing numbers can be preceded by the word "about" or "at least about") of the first solid fraction or a first solid derived from the first solid fraction is, in a second subjecting step, subjected to a third fluid comprising hot compressed water, thereby forming a third mixture, wherein the third mixture comprises a second liquid fraction comprising a second solubilized polyaromatic compound.

In some embodiments, the second subjecting step employs the first solid derived from the first solid fraction, wherein the first solid derived from the first solid fraction is obtained by exposing the first solid fraction to a process selected from the group consisting of acid hydrolysis, enzymatic hydrolysis, sulfur dioxide treatment, hot compressed water treatment, and any combination thereof. In this manner, the first solid fraction is different from the first solid, because the first solid fraction has been treated in a specified manner, thereby forming the first solid derived from the first solid fraction. The treatment comprising hot compressed water can comprise any of the conditions disclosed herein for the subjecting step. In some embodiments, the first solid fraction and the first solid are the same.

As described elsewhere herein, while there may be multiple independent "acidifying" steps (e.g., first, second, etc.) in the methods described herein, the conditions of each "acidifying" step is typically carried out in a general range of conditions. As such, the acidifying step is described herein in general terms, but the ranges for the conditions of each of the "first," "second," etc., acidifying steps can be independently selected from the ranges of conditions generally described herein for the "acidifying step" (i.e., when more than one acidifying step is performed, each acidifying step can be the same or different). Likewise, the acidifying step(s) of the methods described herein can comprise the use of a fluid. The fluid can have any suitable temperature and pressure. While the fluid may have various numeric designations herein (e.g., first, third, etc.), the fluid(s) used in any acidifying step falls within a general range. The conditions described herein for the fluid in an acidifying step can be used to independently define the conditions for the fluid in any acidifying step (e.g., the first, second, etc., acidifying step). The conditions of the fluid in each acidifying step may be the same or different from one another (i.e., they are independent). It will be clear from context whether the fluid or conditions being discussed and claimed herein relates to the subjecting step or the acidifying step.

Any acidifying step (e.g., first, second, etc.) can be performed at any suitable temperature, e.g., 90° C., 100° C., 110° C., 120° C., 130° C., 140° C., 150° C., 160° C., 170° C., 180° C., 190° C., 200° C., 210° C., 220° C., 230° C., 240° C., 250° C., 260° C., 270° C., 280° C., 290° C., or 300° C. Each of the foregoing numbers can be preceded by the word "about," "at least about," or "less than about," and any of the foregoing numbers can be used singly to describe an open-ended range or in combination to describe a close-ended range. Any acidifying step can be carried out in a fluid (e.g., second fluid, fourth fluid, etc.). In some embodiments, the fluid comprises hot compressed water. In some embodiments, the fluid consists of or consists essentially of hot compressed water. As used herein, "carried out in a fluid" means, for example, that in the acidifying step the liquid comprising the solubilized polyaromatic compound can be contacted with a fluid, or the liquid comprising the solubilized polyaromatic compound can be heated to a suitable reaction temperature (such that the acidifying step "is carried out in a fluid" having the specified conditions), or a combination thereof.

Any acidifying step can employ any suitable amount of acid (by weight relative to the total weight of the liquid that is acidified comprising the solubilized polyaromatic compound), such as 0.05 wt. %, 0.1 wt. %, 0.15 wt. %, 0.2 wt. %, 0.25 wt. %, 0.3 wt. %, 0.35 wt. %, 0.4 wt. %, 0.45 wt. %, 0.5 wt. %, 0.55 wt. %, 0.6 wt. %, 0.65 wt. %, 0.7 wt. %, 0.75 wt. %, 0.8 wt. %, 0.85 wt. %, 0.9 wt. %, 0.95 wt. %, 1 wt. %, 1.05 wt. %, 1.1 wt. %, 1.05 wt. %, 1.1 wt. %, 1.15 wt. %, 1.2 wt. %, 1.25 wt. %, 1.3 wt. %, 1.35 wt. %, 1.4 wt. %, 1.45 wt. %, 1.5 wt. %, 1.6 wt. %, 1.7 wt. %, 1.8 wt. %, 1.9 wt. %, 2 wt. %, 2.2 wt. %, 2.4 wt. %, 2.6 wt. %, 2.8 wt. %, 3 wt. %, 3.2 wt. %, 3.4 wt. %, 3.6 wt. %, 3.8 wt. %, 4 wt. %, 4.2 wt. %, 4.4 wt. %, 4.6 wt. %, 4.8 wt. %, 5 wt. %, 5.2 wt. %, 5.4 wt. %, 5.6 wt. %, 5.8 wt. %, or 6 wt. %. Each of the foregoing numbers can be preceded by the word "about," "at least about," or "less than about," and any of the foregoing numbers can be used singly to describe an open-ended range or in combination to describe a close-ended range.

Any acidifying step (e.g., first, second, etc.) can be performed at any suitable pressure, e.g., 1 bar, 2 bar, 5 bar, 10 bar, 15 bar, 20 bar, 25 bar, 30 bar, 35 bar, 40 bar, 45 bar, 50 bar, 60 bar, 70 bar, 80 bar, 90 bar, 100 bar, 110 bar, 120 bar, 130 bar, 140 bar, 150 bar, 175 bar, 200 bar, 225 bar, 250 bar, 275 bar, 300 bar, 325 bar, 350 bar, 375 bar, or 400 bar. Each of the foregoing numbers can be preceded by the word "about," "at least about," or "less than about," and any of the foregoing numbers can be used singly to describe an open-ended range or in combination to describe a close-ended range.

Any acidifying step (e.g., first, second, etc.) can employ any suitable solids content concentration, e.g., 5 g/L, 10 g/L, 15 g/L, 20 g/L, 25 g/L, 30 g/L, 35 g/L, 40 g/L, 45 g/L, 50 g/L, 60 g/L, 70 g/L, 80 g/L, 90 g/L, 100 g/L, 125 g/L, 150 g/L, 175 g/L, 200 g/L, 225 g/L, 250 g/L, 275 g/L, 300 g/L, 325 g/L, 350 g/L, 375 g/L, 400 g/L, 425 g/L, 450 g/L, 475 g/L, or 500 g/L. Each of the foregoing numbers can be preceded by the word "about," "at least about," or "less than about," and any of the foregoing numbers can be used singly to describe an open-ended range or in combination to describe a close-ended range.

Each acidifying step forms a mixture comprising a precipitated polyaromatic compound, and numerical designations are used herein to differentiate the precipitated polyaromatic compound formed in a particular acidifying step. For example in a first acidifying step, a first liquid comprising the first solubilized polyaromatic compound is acidified at a temperature of at least about 90° C., thereby forming a second mixture comprising a first precipitated polyaromatic compound.

In some embodiments, the first mixture obtained in the first subjecting step further comprises a first solid fraction, and at least a portion of the first solid fraction or a first solid derived from the first solid fraction is, in a second subjecting step, subjected to a third fluid comprising hot compressed water, thereby forming a third mixture, wherein the third mixture comprises a second liquid fraction comprising a second solubilized polyaromatic compound. In some embodiments, a second acidifying step is employed. The second acidifying step can be performed on a second liquid comprising the second solubilized polyaromatic compound, in which the second liquid is acidified at a temperature of at least about 90° C., thereby forming a fourth mixture comprising a second precipitated polyaromatic compound. In some embodiments, the second liquid fraction can remain part of the third mixture (which can include a second solid fraction) when the second liquid fraction is acidified in the second acidifying step (i.e., second first liquid fraction is not separated from the second solid fraction, if present, prior to the second acidifying step). In some embodiments, the third mixture further comprises a second solid fraction, and the method further comprises separating at least a portion of the second solid fraction from the second liquid fraction prior to the second acidifying step. In some embodiments, the second liquid fraction (with or without separation from the second solid fraction) is treated in some manner (e.g., concentration, chemical treatment, membrane filtration, etc.), thereby forming a second liquid comprising the second solubilized polyaromatic compound, prior to acidifying the second liquid in the second acidifying step. In this way, "second liquid" can be the same or different from the "second liquid fraction." Separating can be performed by any suitable method known in the art, e.g., filtering, filter press, centrifuge, decanting, cyclone separation, etc., or any combination thereof.

In some embodiments, the methods described herein comprise a collecting step, in which at least a portion of a precipitated polyaromatic compound is collected, thereby obtaining a collected precipitated polyaromatic compound. In embodiments where more than one collecting steps are employed, different numerical designations are used herein to differentiate the collected precipitated polyaromatic compound collected after a particular acidifying step. For example, in a first collecting step (subsequent to or concurrent with the first acidifying step), at least a portion of the first precipitated polyaromatic compound is collected, thereby obtaining a first collected precipitated polyaromatic compound. In some embodiments, a second collecting step is employed, wherein at least a portion of the second precipitated polyaromatic compound is collected, thereby obtaining a second collected precipitated polyaromatic compound.

A substantial portion of a collected precipitated polyaromatic compound obtained in the methods disclosed herein is not discarded, as defined elsewhere herein. For example, a substantial portion of the first collected precipitated polyaromatic compound is not discarded. In some embodiments, a substantial portion of a collected precipitated polyaromatic compound (e.g., first, second, etc.) is not combusted. Combustion is performed in some industrial plants to generate heat for industrial processes. As used herein in this context, a "substantial portion" means at least 30 wt. % (e.g., at least 40 wt. %, 50 wt. %, 60 wt. %, 70 wt. %, 80 wt. %, 90 wt. %, 99 wt. %, or 100 wt. %; each of the foregoing numbers can be preceded by the word term "at least about"), based on the total weight of the collected precipitated polyaromatic compound.

In some embodiments, at least a portion of the collected precipitated polyaromatic compound (e.g., first, second, etc.) from any acidifying step is sold, bartered, traded, or any combination thereof. For example, the collected precipitated polyaromatic compound can be sold in exchange for monetary payment. In some embodiments, the collected precipitated polyaromatic compound can be bartered for a good, a service, or both. In some embodiments, the collected precipitated polyaromatic compound can be traded for money, a good, a service, or any combination thereof. For example, at least a portion of the first collected precipitated polyaromatic compound is sold, bartered, traded, or any combination thereof. For example, at least a portion of the second collected precipitated polyaromatic compound is sold, bartered, traded, or any combination thereof.

In some embodiments, at least a portion of the collected precipitated polyaromatic compound from any acidifying step is incorporated into a product capable of sale, barter, trade, or any combination thereof. As used herein, "capable of sale, barter, trade, or any combination thereof" means that the product is capable of being, but is not necessarily, sold, bartered, traded, or any combination thereof. For example, at least a portion of the first collected precipitated polyaromatic from the first collecting step is incorporated into a product capable of sale, barter, trade, or any combination thereof. In some embodiments, provided is the product capable of sale, barter, trade, or any combination thereof, in which at least a portion of the first collected precipitated polyaromatic from the first collecting step has been incorporated. In some embodiments, at least a portion of the second collected precipitated polyaromatic from the second collecting step is incorporated into a product capable of sale, barter, trade, or any combination thereof. In some embodiments, provided is the product capable of sale, barter, trade, or any combination thereof, in which at least a portion of the second collected precipitated polyaromatic from the second collecting step has been incorporated. The product capable of sale, barter, trade, or any combination thereof can be any suitable product. For example, the product can be an adhesive (e.g., phenol-formaldehyde resin), a thermoplastic (e.g., polyethylene, polypropylene, or a combination thereof), etc.

In some embodiments, the precipitated polyaromatic compound (e.g., first, second, etc.) from any acidifying step (e.g., first, second, etc.) is a compound selected from the group consisting of lignin, pseudolignin, a polyfuranic compound, and any combination thereof.

In some embodiments, the liquid comprising a solubilized polyaromatic compound that is subjected to an acidifying step does not comprise spent liquor. For example, in some embodiments the first liquid (or second liquid) comprising the first (or second) solubilized polyaromatic compound does not comprise or consist of spent liquor.

In some embodiments, two subjecting steps, two acidifying steps, and two collecting steps are employed, and the two resulting collected precipitated polyaromatic compounds are combined.

FIG. 1 depicts a combination of several embodiments of the methods described herein. The description of FIG. 1 set forth hereinbelow is meant to be illustrative only, and the various options and permutations as described elsewhere herein apply to FIG. 1. Lignocellulosic biomass (101) (i.e., the first biomass) is, in a subjecting step (102) (i.e., the first subjecting step), subjected to a fluid (i.e., the first fluid) comprising hot compressed water, thereby forming a mixture (103) (i.e., the first mixture). In some embodiments, the first biomass is raw biomass, biomass obtained by a process as described elsewhere herein, or a combination thereof. The first mixture (103) typically comprises a first liquid fraction (which comprises a first solubilized polyaromatic compound) and a first solid fraction. A first liquid (which may be the same or different from the first liquid fraction) comprising the first solubilized polyaromatic compound is, in a first acidifying step (104), acidified at a temperature of at least about 90° C., thereby forming a second mixture (105) comprising a first precipitated polyaromatic compound. The first liquid comprising the first solubilized polyaromatic compound may be (i) the first liquid fraction present as part of the first mixture when acidified, (ii) the first liquid fraction that has been separated from the first solid fraction, (iii) a first liquid that has been treated in one or more ways but still contains the solubilized polyaromatic compound (for example, the first liquid fraction may be separated from the first solid fraction and then concentrated via evaporation, resulting in a first liquid that contains the first solubilized polyaromatic compound but is nevertheless technically different from the first liquid fraction resulting from the subjecting step), or (iv) any combination thereof. In a first collecting step (106), at least a portion of the first precipitated polyaromatic compound is collected, thereby obtaining a first collected precipitated polyaromatic compound (107). Typically, a substantial portion of the first collected precipitated polyaromatic compound is not discarded.

Optionally (as indicated by the dotted line in FIG. 1), at least a portion of the first solid fraction, or a first solid derived from the first solid fraction, is, in a second subjecting step (108), subjected to a third fluid comprising hot compressed water, thereby forming a third mixture (109). In some embodiments, the first solid fraction is carried on to the second subjecting step (108). In some embodiments, the first solid fraction is treated in some manner (e.g., acid hydrolysis, enzymatic hydrolysis, sulfur dioxide treatment, hot compressed water treatment, organic solvent extraction, etc.) to form a first solid, and the first solid fraction carried on to the second subjecting step (108). In some embodiments, the third mixture (109) comprises a second liquid fraction (which comprises a second solubilized polyaromatic compound) and a second solid fraction. A second liquid (which may be the same or different from the second liquid fraction) comprising the second solubilized polyaromatic compound is, in a second acidifying step (110), acidified at a temperature of at least about 90° C., thereby forming a fourth mixture (111) comprising a second precipitated polyaromatic compound. The second liquid comprising the second solubilized polyaromatic compound may be (i) the second liquid fraction present as part of the third mixture when acidified, (ii) the second liquid fraction that has been separated from the second solid fraction, (iii) a second liquid that has been treated in one or more ways but still contains the solubilized polyaromatic compound (for example, the second liquid fraction may be separated from the second solid fraction and then concentrated via evaporation, resulting in a second liquid that contains the first solubilized polyaromatic compound but is nevertheless technically different from the second liquid fraction resulting from the subjecting step), or (iv) any combination thereof. In a second collecting step (112), at least a portion of the second precipitated polyaromatic compound is collected, thereby obtaining a second collected precipitated polyaromatic compound (113). Typically, a substantial portion of the second collected precipitated polyaromatic compound is not discarded.

The precipitated polyaromatic compound obtained from any acidifying step can have any of the characteristics described herein, or any combination of the characteristics described herein. In some embodiments, the polyaromatic compound (e.g., precipitated polyaromatic compound) is present in a product capable of sale, barter, trade, or any combination thereof, and, prior to incorporation into the product, the polyaromatic compound can have the characteristics described herein, or any combination of the characteristics described herein. In some embodiments, the polyaromatic compound (e.g., precipitated polyaromatic compound) can have the characteristic described herein, or any combination thereof, after incorporation into a product capable of sale, barter, trade, or any combination thereof.

The structure of the precipitated polyaromatic compound can be determined using nuclear magnetic resonance (NMR)

methods, and the structural characteristic can be described in terms of the amounts of moieties expressed as units of moiety per 100 aromatic units ("units per 100 Ar"), and can be considered as mol %. These features are measured using the NMR methods described herein and set forth in U.S. Patent Application Publication 2014/0275501, hereby incorporated by reference in its entirety. To determine the amount of moiety per 100 Ar, the aromatic region (about 100-162 ppm) in the $^{13}C$ spectrum is integrated, and this integral set to a value of 600. Subsequent integration of the moieties or regions of interest in this same spectrum will now be in the units of "per 100 Ar." The unit of measurement "units per 100 Ar" is well known in the art and is the conventional way for describing moieties of lignin (a polyaromatic compound, as defined herein). The measurements can be conducted by quantitative NMR, such as quantitative $^{13}C$ NMR spectroscopy. See, for example, Capanema, E. A., Balakshin, M. Yu., Chang, H-m., Jameel, H. (2005) Isolation and characterization of residual lignins from hardwood pulps: Method improvements. Proc. 13th Intern. Symp. Wood Fibre Pulping C, Auckland, New Zealand, v.III, 57-64, incorporated herein by reference in its entirety, for further information on calculating the amounts of moieties in polyaromatic compounds (e.g., lignin). Quantifying the amounts of the various moieties present via $^{13}C$ and/or $^1H$ NMR spectroscopy typically requires integration of the $^{13}C$ and/or $^1H$ NMR spectra. Chemical shift ranges where various moieties or other regions of interest may be located in a $^{13}C$ and/or $^1H$ spectrum are reported herein to aid in determining the measurement of these various moieties. However, as one of ordinary skill in the art would certainly understand, the actual integral may be located within a slightly different chemical shift range, and one of ordinary skill in the art would be able to recognize this fact and be able to integrate the appropriate peaks in the appropriate chemical shift range to determine as accurately as possible the integrals of various moieties or regions of interest. Examples of structural features of the precipitated polyaromatic compound include, e.g., CO, COOR, OH, S/G, ArH, DC, β-O-4, β-β, β-5, OCH3, and aliphatic contents.

In the measurement of some structural moieties, it is sometimes useful to acetylate the polyaromatic compound (e.g., lignin) for analytical purposes. In particular, acetylation is used to quantify various OH groups of polyaromatic compound. In addition, polyaromatic compound acetylation can result in separation of some signals in an NMR spectrum that otherwise overlap, thereby allowing more accurate integration and quantification. Acetylation can be performed by the method disclosed in Adler, E. et al. (1987), Holzforschung, 41, 199-207, "Investigation of the acid catalyzed alkylation of lignin by means of NMR spectroscopic methods" hereby incorporated by reference in its entirety.

The precipitated polyaromatic compound can have different types of carbonyl ("CO") moieties, and these moieties can be measured from the regions of about 200-215 ppm and about 185-200 ppm for non-conjugated and conjugated CO, respectively, in a $^{13}C$ NMR spectrum. Typically, the total CO content, non-conjugated CO content, and conjugated CO content are measured for acetylated polyaromatic compound and non-acetylated polyaromatic compound, and the two values are averaged. Total CO content is the sum of conjugated CO and non-conjugated CO.

The total carbonyl ("CO") content of the precipitated polyaromatic compound typically is at least about 24 units per 100 Ar, e.g., at least about 26, 28, 30, 32, 34, 36, 38, 40, 42, 44, 46, 48, 50, 52, 54, 56, 58, 60, 65, 70, 75, 80, 85, 90, 95, 100, 105, 110, or 120 (each of the foregoing numbers is preceded by the phrase "at least about") per 100 Ar. The maximum total carbonyl content of the precipitated polyaromatic compound is not particularly important, but typically is less than about 130 units per 100 Ar, e.g., less than about 120, 110, 105, 100, 95, 90, 85, 80, 75, 70, 65, 60, 58, 56, 54, 52, 50, 48, 46, 44, 42, 40, 38, 36, 34, 32, or 30 (each of the foregoing numbers is preceded by the phrase "less than about") per 100 Ar. Any of the foregoing endpoints can be combined to describe a close-ended range, or the endpoints can singly describe an open-ended range.

The non-conjugated carbonyl ("CO") content of the precipitated polyaromatic compound typically is at least about 10 units per 100 Ar, e.g., at least about 12, 14, 15, 16, 17, 18, 19, 20, 22, 24, 26, 28, 30, 32, 34, 36, 38, 40, 42, 44, 46, 48, 50, 55, 60, 65, 70, 80, 90, 100, 110, 120, 130, 140, or 150 (each of the foregoing numbers is preceded by the phrase "at least about") per 100 Ar. The maximum non-conjugated carbonyl content of the precipitated polyaromatic compound is not particularly important, but typically is less than about 160 units per 100 Ar, e.g., less than about 150, 140, 130, 120, 110, 100, 90, 80, 70, 65, 60, 55, 50, 48, 46, 44, 42, 40, 38, 36, 34, 32, 30, 28, 26, 24, 22, 20, 19, 18, 17, 16, 15, 14, or 12 (each of the foregoing numbers is preceded by the phrase "less than about") per 100 Ar. Any of the foregoing endpoints can be combined to describe a close-ended range, or the endpoints can singly describe an open-ended range.

The conjugated carbonyl ("CO") content of the precipitated polyaromatic compound typically is at least about 9 units per 100 Ar, e.g., at least about 10, 11, 12, 13, 14, 15, 16, 18, 20, 22, 24, 26, 28, 30, 35, 40, 45, 50, 55, or 60 (each of the foregoing numbers is preceded by the phrase "at least about") per 100 Ar. The maximum conjugated carbonyl content of the precipitated polyaromatic compound is not particularly important, but typically is less than about 65 units per 100 Ar, e.g., less than about 60, 55, 50, 45, 40, 35, 30, 28, 26, 24, 22, 20, 18, or 16 (each of the foregoing numbers is preceded by the phrase "less than about") per 100 Ar. Any of the foregoing endpoints can be combined to describe a close-ended range, or the endpoints can singly describe an open-ended range.

Hydroxyl ("OH") moieties can be measured from the resonance at about 165-171.5 ppm in the $^{13}C$ NMR spectra of acetylated polyaromatic compound preparations. However, the resonance of acetyl groups may be somewhat overlapped with the resonance of COOR groups, especially for primary OH groups. Therefore, for more accurate values, the resonance of signals in the spectra of non-acetylated polyaromatic compound are subtracted from the corresponding resonance in the spectra of the acetylated polyaromatic compound in the range of about 165-169 ppm for phenolic OH groups. Phenolic OH content can be calculated according to the following equation:

$$\text{phenolic OH content} = I(169.0-165.0)ac - I(169.0-165.0)na$$

where I(xx-xx)ac and I(xx-xx)nc are the integrals in the range of xx-xx ppm in the $^{13}C$ NMR spectra of acetylated ("ac") and non-acetylated polyaromatic compounds ("na"), respectively The phenolic hydroxyl ("OH") content of the precipitated polyaromatic compound typically is at least about 70 units per 100 Ar, e.g., at least about 72, 74, 76, 78, 80, 82, 84, 86, 88, 90, 92, 94, 96, 98, 100, 105, 110, 115, 120, 125, 130, 135, 140, 145, or 150 (each of the foregoing numbers is preceded by the phrase "at least about") per 100 Ar. The maximum phenolic OH content of the precipitated polyaromatic compound is not particularly important, but typically is less than about 155 units per 100 Ar, e.g., less than about 150, 145, 140, 135, 130, 125, 120, 115, 110, 100, 98, 96, 94, 92, 90, 88, 86, 84, 82, 80, 78, 76, 74, or 72 (each of the foregoing numbers is preceded by the phrase "less than about") per 100 Ar. Any of the foregoing endpoints can be combined to describe a close-ended range, or the endpoints can singly describe an open-ended range.

The methoxyl ("OCH$_3$") content can be measured using the integrals at about 54.3-58.5 ppm in the $^{13}$C spectra. Typically, the OCH$_3$ content is measured for both acetylated and non-acetylated polyaromatic compounds, and the two values are averaged. The minimum methoxyl ("OCH$_3$") content of the precipitated polyaromatic compound is not particularly important, but typically is at least about 30 units per 100 Ar, e.g., at least about 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 105, 110, 115, 120, or 125 (each of the foregoing numbers is preceded by the phrase "at least about") per 100 Ar. The maximum methoxyl content of the precipitated polyaromatic compound typically is less than about 130 units per 100 Ar, e.g., less than about 125, 120, 115, 110, 105, 100, 98, 96, 94, 92, 90, 88, 86, 84, 82, 80, 78, 76, 74, 72, 70, 68, 66, 64, 62, 60, 58, 56, 54, 52, 50, 48, 46, 44, 42, 40, 38, 36, 34, or 32 (each of the foregoing numbers is preceded by the phrase "less than about") per 100 Ar. Any of the foregoing endpoints can be combined to describe a close-ended range, or the endpoints can singly describe an open-ended range.

The oxygenated aliphatic content can be measured using the integrals at about 58.5-90.0 ppm in the spectra of both the acetylated and non-acetylated polyaromatic compound, and the results are averaged. When sugar content is at least about 4 units per 100 Ar in an NMR spectrum of a polyaromatic compound, the oxygenated aliphatic content typically is corrected for sugar content according to the method discussed below (since these signals may overlap somewhat with the signals for certain functional groups, for example, various types of OH moieties and oxygenated aliphatic moieties). It is therefore sometimes desirable to correct for this sugar content. In the spectra of non-acetylated polyaromatic compound, sugar signals are partially overlapped with strong signals of S-2,6. However, after acetylation, the C-1 signals of carbohydrates are shifted upheld and can be separated from the polyaromatic compound signals. Total amount of sugars can be estimated from the integral at about 99-102 ppm in the $^{13}$C NMR spectra of acetylated polyaromatic compound. These values agree quite well with the values obtained by sugar analysis using wet chemistry methods. The corrections for sugar content can be made as follows:

OHpr-cor=OHpr−Sugars×% Hexose/100

OHsec-cor=OHsec−2Sugars

Oxygenated Aliphatic=I(90-58)cor=I(90-58)−Sugars×(4% Xyl+5% Hexose)/100 in which "OHpr-cor" is the amount of primary aliphatic OH groups corrected for sugar content, "OHpr" is the amount of primary aliphatic OH groups not corrected for sugar content, "Sugars" is the amount of sugars in the polyaromatic compound sample per 100 Ar, "% Hexose" is the percentage of hexoses in sugars per total sugar content, "% Xyl" is the percentage of xylan in sugars per total sugar content, "OHsec-cor" is the amount of secondary aliphatic OH groups corrected for sugar content, "OHsec" is the amount of secondary aliphatic OH groups not corrected for sugar content, "Oxygenated Aliphatic" is the amount of oxygenated aliphatic carbons in polyaromatic compound, "I(90-58) cor" is the integral at about 90-58 ppm corrected for sugar content, and "I (90-58)" is the integral at 90-58 ppm not corrected for sugar content. % Hexose and % Xyl were measure according to NREL/TP-510-42618.

The oxygenated aliphatic content of the precipitated polyaromatic compound after correction for sugar content (if sugar content is above 2 units per 100 Ar) typically is at least about 34 units per 100 Ar, e.g., at least about 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 105, 110, or 115 (each of the foregoing numbers is preceded by the phrase "at least about") per 100 Ar. The maximum oxygenated aliphatic content of the precipitated polyaromatic compound (corrected for sugar content if sugar content is above 2 units per 100 Ar) is not particularly important, but typically is less than about 120 units per 100 Ar, e.g., less than about 115, 110, 105, 100, 98, 96, 94, 92, 90, 88, 86, 84, 82, 80, 78, 76, 74, 72, 70, 68, 66, 64, 62, 60, 58, 56, 54, 52, 50, 48, 46, 44, 42, 40, 38, or 36 (each of the foregoing numbers is preceded by the phrase "less than about") per 100 Ar. Any of the foregoing endpoints can be combined to describe a close-ended range, or the endpoints can singly describe an open-ended range.

The ratio of syringyl to guaiacyl ("S/G ratio") can be measured by $^{13}$C NMR using acetylated polyaromatic compound. The amount of syringyl (S) can be measured by integrating the signals corresponding to the 2- and 6-positions of the syringyl unit (i.e., $S_{2,6}$) in the chemical shift range of about 100-108.6 ppm, and dividing the integral by two (i.e., $S_{2,6}/2$). The amount of guaiacyl can be measured by integrating the 2-position of guaiacyl (i.e., $G_2$) in the chemical shift range of about 108.6-114.6 ppm. The S/G ratio can then be calculated as follows: S/G ratio=$(S_{2,6}/G_2)/2$.

The minimum S/G ratio of the polyaromatic compound typically is not particularly important, but typically is at least about 0.2, e.g., at least about 0.25, 0.3, 0.35, 0.4, 0.45, 0.5, 0.55, 0.6, 0.65, 0.7, 0.75, 0.8, 0.85, 0.9, 0.95, 1, 1.05, 1.1, 1.15, 1.2, or 1.25 (each of the foregoing numbers is preceded by the phrase "at least about"). The maximum S/G ratio of the precipitated polyaromatic compound is not particularly important, but typically is less than about 1.8, e.g., less than about 1.6, 1.5, 1.4, 1.3, 1.25, 1.2, 1.15, 1.1, 1.05, 1, 0.95, 0.9, 0.85, 0.8, 0.75, 0.7, 0.65, 0.6, 0.55, 0.5, 0.45, 0.4, 0.35, 0.3, or 0.25 (each of the foregoing numbers is preceded by the phrase "less than about"). Any of the foregoing endpoints can be combined to describe a close-ended range, or the endpoints can singly describe an open-ended range.

The degree of condensation ("DC") of the polyaromatic compound can be measured by $^{13}$C NMR using non-acetylated polyaromatic compound and the formula: DC=[300−(S+H)/(S+G+H)*100]−$I_{100-125}$. S and G in this formula are the same as defined in the calculation of the S/G ratio. H is determined by integrating in the chemical shift range of about 156-161 ppm. The DC can be thought of as the percentage of condensed moieties (condensed C9 units) to total moieties (all C9 units). The DC of the polyaromatic compound typically is at least about 40, e.g., at least about 42, 44, 46, 48, 50, 52, 54, 56, 58, 60, 62, 64, 66, 68, 70, 72, 74, 76, 78, 80, 82, 84, 86, 88, 90, 92, 94, 96, 98, or 100 (each of the foregoing numbers is preceded by the phrase "at least about"). The maximum DC of the precipitated polyaromatic compound is not particularly important, but typically is less than about 102, e.g., less than about 100, 98, 96, 94, 92, 90, 88, 86, 84, 82, 80, 78, 76, 74, 72, 70, 68, 66, 64, 62, 60, 58, 56, 54, 52, 50, 48, 46, 44, or 42 (each of the foregoing numbers is preceded by the phrase "less than about"). Any of the foregoing endpoints can be combined to describe a close-ended range, or the endpoints can singly describe an open-ended range.

β-O-4 linkages can be measured by subtracting the resonance at about 83-90 ppm in the $^{13}$C NMR spectrum of an acetylated polyaromatic compound from the resonance in the same region in the spectrum of the corresponding non-acetylated polyaromatic compound. The content of β-O-4 linkages of the polyaromatic compound typically can range from a trace amount, or may be at least about 1 unit per 100 Ar, e.g., at least about 2, 3, 4, 5, 6, 8, 10, 12, 14, 16, or 18 (each of the foregoing numbers is preceded by the phrase "at least about") per 100 Ar. The maximum content of β-O-4 linkages is not particularly important, but typically is less than about 20 units per 100 Ar, e.g., less than about 18, 16, 14, 12, 10, 8, 6, 5, 4, 3, 2, or 1 (each of the foregoing numbers is preceded by the phrase "less than about") per 100 Ar. Any of the foregoing endpoints can be combined to describe a close-ended range, or the endpoints can singly describe an open-ended range. In some embodiments, β-O-4 linkages are only present in the polyaromatic compound in trace amounts (e.g., less than about 1 units per 100 Ar).

In some embodiments, provided is a product capable of sale, barter, trade, or any combination thereof comprising a polyaromatic compound, wherein, prior to incorporation of the polyaromatic compound into the product, the polyaromatic compound has at least one of the following features: (a) a total carbonyl content of at least about 36 units, per 100 aromatic units, (b) a non-conjugated carbonyl content of at least about 17 units, per 100 aromatic units, (c) a conjugated carbonyl content of at least about 12 units, per 100 aromatic units, (d) a methoxyl content of less than about 110 units, per 100 aromatic units, and (e) any combination of features (a) through (d). In some embodiments, the product capable of sale, barter, trade, or any combination thereof comprises a polyaromatic compound, wherein, prior to incorporation of the polyaromatic compound into the product, the polyaromatic compound is characterized by one of the following: (i) a combination of features (a) and (b); (ii) a combination of feature (a) and (c); (iii) a combination of features (a) and (d); (iv) a combination of features (b) and (c); (v) a combination of features (b) and (d); (vi) a combination of features (c) and (d); (vii) a combination of features (a), (b), and (c); (viii) a combination of features (a), (b), and (d); (ix) a combination of features (a), (c), and (d); (x) a combination of features (b), (c), and (d); (xi) a combination of features (a), (b), (c), and (d). In some embodiments, the polyaromatic compound in any of the foregoing embodiments of this paragraph (or any other paragraph herein) can have at least one of the following features: (1) a methoxyl content of less than about 110 units, per 100 aromatic units; and (2) an S/G ratio of less than about 1.60.

Some embodiments of the invention are set forth in the following clauses, and any combination of these clauses, or portions of these clauses, may be made to define an embodiment of the invention.

Clause 1: a method comprising a first subjecting step, wherein a first biomass is subjected to a first fluid comprising hot compressed water, thereby forming a first mixture; wherein the first mixture comprises a first liquid fraction comprising a first solubilized polyaromatic compound; a first acidifying step, wherein a first liquid comprising the first solubilized polyaromatic compound is acidified at a temperature of at least about 90° C., thereby forming a second mixture comprising a first precipitated polyaromatic compound; and a first collecting step, wherein at least a portion of the first precipitated polyaromatic compound is collected, thereby obtaining a first collected precipitated polyaromatic compound; wherein a substantial portion of the first collected precipitated polyaromatic compound is not discarded.

Clause 2: the method of clause 1, wherein at least a portion of the first collected precipitated polyaromatic compound is sold, bartered, traded, or any combination thereof.

Clause 3: the method of clause 1 or clause 2, wherein at least a portion of the first collected precipitated polyaromatic compound is incorporated into a product capable of sale, barter, trade, or any combination thereof.

Clause 4: the method of any one of clauses 1-3, wherein a substantial portion of the first collected precipitated polyaromatic compound is not combusted.

Clause 5: the method of any one of clauses 1-4, wherein the first precipitated polyaromatic compound is selected from the group consisting of lignin, pseudolignin, a polyfuranic compound, and any combination thereof.

Clause 6: the method of any one of clauses 1-5, wherein the first mixture further comprises a first solid fraction, and the method further comprises separating at least a portion of the first solid fraction from the first liquid fraction prior to the first acidifying step.

Clause 7: the method of any one of clauses 1-6, wherein the first fluid is substantially free of added acid.

Clause 8: the method of any one of clauses 1-7, wherein the first acidifying step is carried out in a second fluid comprising hot compressed water.

Clause 9: the method of any one of clauses 1-8, wherein the first fluid has a temperature of about 130° C. to about 374° C.

Clause 10: the method of any one of clauses 1-8, wherein the hot compressed water in the first fluid is supercritical water.

Clause 11: the method of any one of clauses 1-10, wherein the first fluid consists essentially of hot compressed water.

Clause 12: the method of any one of clauses 1-11, wherein the first liquid comprising the first solubilized polyaromatic compound does not comprise spent liquor.

Clause 13: the method of any one of clauses 1-12, wherein the first biomass is raw biomass.

Clause 14: the method of any one of clauses 1-13, wherein the first biomass is obtained by a process selected from the group consisting of acid hydrolysis, enzymatic hydrolysis, sulfur dioxide treatment, hot compressed water treatment, and any combination thereof.

Clause 15: the method of any one of clauses 1-14, wherein the first mixture further comprises a first solid fraction, and at least a portion of the first solid fraction or a first solid derived from the first solid fraction is, in a second subjecting step, subjected to a third fluid comprising hot compressed water, thereby forming a third mixture, wherein the third mixture comprises a second liquid fraction comprising a second solubilized polyaromatic compound.

Clause 16: the method of clause 15, wherein the third fluid is substantially free of added acid.

Clause 17: the method of clause 15 or clause 16, wherein the third fluid has a temperature of about 130° C. to about 374° C.

Clause 18: the method of clause 15 or clause 16, wherein the hot compressed water in the third fluid is supercritical water.

Clause 19: the method of any one of clauses 15-18, wherein the third fluid consists essentially of hot compressed water.

Clause 20: the method of any one of clauses 15-19, wherein the second subjecting step employs the first solid derived from the first solid fraction, wherein the first solid derived from the first solid fraction is obtained by exposing the first solid fraction to a process selected from the group consisting of acid hydrolysis, enzymatic hydrolysis, sulfur dioxide treatment, hot compressed water treatment, and any combination thereof.

Clause 21: the method of any one of clauses 15-20, further comprising a second acidifying step, wherein a second liquid comprising the second solubilized polyaromatic compound is acidified at a temperature of at least about 90° C., thereby forming a fourth mixture comprising a second precipitated polyaromatic compound; and a second collecting step, wherein at least a portion of the second precipitated polyaromatic compound is collected, thereby obtaining a second collected precipitated polyaromatic compound; wherein a substantial portion of the second collected precipitated polyaromatic compound is not discarded.

Clause 22: the method of clause 21, wherein at least a portion of the second collected precipitated polyaromatic compound is sold, bartered, traded, or any combination thereof.

Clause 23: the method of clause 21 or clause 22, wherein at least a portion of the second collected precipitated polyaromatic compound is incorporated into a product capable of sale, barter, trade, or any combination thereof.

Clause 24: the method of any one of clauses 21-23, wherein a substantial portion of the second collected precipitated polyaromatic compound is not combusted.

Clause 25: the method of any one of clauses 21-24, wherein the second precipitated polyaromatic compound is selected from the group consisting of lignin, pseudolignin, a polyfuranic compound, and any combination thereof.

Clause 26: the method of any one of clauses 21-25, wherein the third mixture further comprises a second solid fraction, and the method further comprises separating at least a portion of the second solid fraction from the second liquid fraction prior to the second acidifying step.

Clause 27: the method of any one of clauses 21-26, wherein the second acidifying step is carried out in a fourth fluid comprising hot compressed water.

Clause 28: the method of any one of clauses 21-27, wherein the second liquid comprising the second solubilized polyaromatic compound does not comprise spent liquor.

Clause 29: the product of any one of clauses 3-28.

Clause 30: the product of clause 3 or clause 23.

Clause 31: a product capable of sale, barter, trade, or any combination thereof comprising a polyaromatic compound, wherein, prior to incorporation of the polyaromatic compound into the product, the polyaromatic compound has: a total carbonyl content of at least about 36 units, per 100 aromatic units.

Clause 32: a product capable of sale, barter, trade, or any combination thereof comprising a polyaromatic compound, wherein, prior to incorporation of the polyaromatic compound into the product, the polyaromatic compound has: a non-conjugated carbonyl content of at least about 17 units, per 100 aromatic units.

Clause 33: a product capable of sale, barter, trade, or any combination thereof comprising a polyaromatic compound, wherein, prior to incorporation of the polyaromatic compound into the product, the polyaromatic compound has: conjugated carbonyl content of at least about 12 units, per 100 aromatic units.

Clause 34: a product capable of sale, barter, trade, or any combination thereof comprising a polyaromatic compound, wherein, prior to incorporation of the polyaromatic compound into the product, the polyaromatic compound has: a methoxyl content of less than about 110 units, per 100 aromatic units.

Clause 35: the product of any one of clauses 31-34, wherein the polyaromatic compound is lignin or pseudolignin.

Clause 36: the product of any one of clauses 32-34, wherein, prior to incorporation of the polyaromatic compound into the product, the polyaromatic compound has: a total carbonyl content of at least about 36 units, per 100 aromatic units.

Clause 37: the product of any one of clauses 31, 33, or 34, wherein, prior to incorporation of the polyaromatic compound into the product, the polyaromatic compound has: a non-conjugated carbonyl content of at least about 17 units, per 100 aromatic units.

Clause 38: the product of any one of clauses 31, 32, or 34, wherein, prior to incorporation of the polyaromatic compound into the product, the polyaromatic compound has: a conjugated carbonyl content of at least about 12 units, per 100 aromatic units.

Clause 39: the product of any one of clauses 31, 32, or 33, wherein prior to incorporation of the polyaromatic compound into the product, the polyaromatic compound has: a methoxyl content of less than about 110 units, per 100 aromatic units.

Clause 40: the product of any one of clauses 1-34, wherein prior to incorporation of the polyaromatic compound into the product, the polyaromatic compound has: an S/G ratio of less than about 1.60.

Clause 41: a product capable of sale, barter, trade, or any combination thereof comprising a polyaromatic compound, wherein, prior to incorporation of the polyaromatic compound into the product, the polyaromatic compound has: a total phenolic hydroxyl content of at least about 80 units, per 100 aromatic units.

Clause 42: the product of any one of clauses 1-34, wherein prior to incorporation of the polyaromatic compound into the product, the polyaromatic compound has: a total phenolic hydroxyl content of at least about 80 units, per 100 aromatic units.

The invention is further illustrated by the following examples, in which all parts and percentages are by weight, unless otherwise stated. It should be understood that these examples, while indicating preferred embodiments of the invention, are given by way of illustration only and are not to be construed as limiting in any manner. From the above discussion and these examples, one skilled in the art can ascertain the essential characteristics of this invention, and without departing from the spirit and scope thereof, can make various changes and modifications of the invention to adapt it to various usages and conditions.

EXAMPLES

Compositional analysis was performed according to the standard National Renewable Energy Laboratory (NREL) protocol for biomass analysis (NREL/TP-510-42618, herein incorporated by reference in its entirety). The sugars listed in Table 1 are xylan, glucan, arabinan, galactan, rhamnan, and mannan.

Structural analysis, as reported in Table 2, was performed as follows. NMR spectra were recorded on a Bruker AVANCE 500 MHz spectrometer at 300 K using DMSO-d6 as the solvent. Chemical shifts were referenced to trimethylsilane (TMS) (0.0 ppm). For the quantitative $^{13}$C-NMR, the concentration of polyaromatic compound was 35% (w/v); a 90° pulse width, a 1.4 second acquisition time and 1.7 second relaxation delay were used. Chromium (III) acetylacetonate (0.016M) was added to the polyaromatic compound solution to provide complete relaxation of all nuclei. A total of 20,000 scans were collected. The spectra were processed and the data are calculated according to previously published procedure (Capanema, E. A., Balakshin, M. Yu., Chang, H-m., Jameel, H. (2005) Isolation and characterization of residual lignins from hardwood pulps: Method improvements. Proc. 13th Intern. Symp. Wood Fibre Pulping C, Auckland, New Zealand, v.III, 57-64, incorporated herein by reference in its entirety). The CO, COOR, OH, S/G, ArH, DC, β-O-4, β-β, β-5, OCH3, and aliphatic contents are measured by quantitative $^{13}$C NMR and are in the units "per 100 aromatic rings." These features are measured using the NMR methods described herein and set forth in U.S. Patent Application Publication 2014/0275501, hereby incorporated by reference in its entirety.

For example, the amounts of moieties are expressed as units of moiety per 100 aromatic units ("units per 100 Ar"), and can be considered as mol %. The aromatic region (about 100-162 ppm) in the $^{13}$C spectrum is integrated, and this integral set to a value of 600. Subsequent integration of the moieties or regions of interest in this same spectrum will now be in the units of "per 100 Ar." The unit of measurement "units per 100 Ar" is well known in the art and is the conventional way for describing moieties of lignin (e.g., polyaromatic compound). The measurements can be conducted by quantitative nuclear magnetic resonance spectroscopy (NMR), such as quantitative $^{13}$C NMR spectroscopy. See, for example, Capanema and Jameel et al. (2005) for further information on calculating the amounts of moieties in lignin. Quantifying the amounts of the various moieties present in polyaromatic compound via $^{13}$C and/or $^{1}$H NMR spectroscopy typically requires integration of the $^{13}$C and/or $^{1}$H NMR spectra. Chemical shift ranges where various polyaromatic compound moieties or other regions of interest may be located in a $^{13}$C and/or $^{1}$H spectrum are reported herein to aid in determining the measurement of these various moieties. However, as one of ordinary skill in the art would certainly understand, the actual integral may be located within a slightly different chemical shift range, and one of ordinary skill in the art would be able to recognize this fact and be able to integrate the appropriate peaks in the appropriate chemical shift range to determine as accurately as possible the integrals of various moieties or regions of interest.

Example 1

This example demonstrates one embodiment of the production and collection of polyaromatic compound. Size-reduced (<800 μm average particle size) biomass comprising lignocellulosic hardwood was mixed with water to form a slurry. The slurry was reacted at a temperature of about 170-245° C. and a pressure of about 35-62 bar for a period of about 1-120 minutes. The reaction mixture was cooled to less than 100° C. and depressurized to less than 10 bar. The cooled and depressurized reaction mixture was then filtered using a filter press. The recovered solids were employed in Example 2. The liquids correspond to the xylo-oligosaccharide (XOS) stream.

The XOS stream was acidified under the following conditions: 95-150° C., 0.1-6% sulfuric acid, 10-500 g/L oligomer, 5 min to 5 hours. The precipitated material (polyaromatic compound (PAC-1)) was collected by filtration, re-slurried in water to form a fine suspension, filtered, exhaustively washed on the filter with water, dried, and then analyzed. The compositional and structural analyses of PAC-1 are shown in Tables 1 and 2, respectively.

TABLE 1

Compositional analysis of PAC-1

| Sample | % Ash | % Xyl | % Glu | % Ara | % Gal | % Rha | % Man | Total sugar % | Total polyaromatic % | Total % |
|---|---|---|---|---|---|---|---|---|---|---|
| PAC-1 | 0.01 | 1.1 | 0.2 | <0.1 | <0.1 | <0.1 | 0.19 | 1.7 | 91.1 | 92.7 |

Example 2

This example demonstrates one embodiment of the production and collection of polyaromatic compound. The recovered solids from Example 1 were re-slurried with water and the slurry pumped at a rate of about 160 kg/h to about 200 kg/h (as measured at ambient conditions), while sub-critical, near-critical, or supercritical water having a temperature of about 360° C. to about 600° C. and a pressure of about 200 bar to about 600 bar was contacted with the slurry at a rate of about 485 kg/h to about 505 kg/h (termed "the SH process"). Reaction temperature was about 365° C. to about 450° C., and the residence time at reaction temperature was less than about 10 sec, typically less than about 3 sec. The resulting reaction mixture was cooled to ambient conditions, and the mixture subjected to a filter press to obtain solids and a liquid gluco-oligosaccharide (GOS) stream.

The GOS stream was acidified under the following conditions: 95-150° C., 0.1-6% sulfuric acid, 10-500 g/L oligomer, 5 min to 5 hours. The precipitated material (polyaromatic compound (PAC 2)) was cooled to about 60° C. or less while stirring, and the cooled mixture filtered through a 25 micron bag filter, with the PAC-2 material captured in the bag. PAC-2 was re-slurried in water to form a fine suspension, filtered, exhaustively washed on the filter with water, dried, and then analyzed. The structural analysis of PAC-2 is shown in Table 2.

TABLE 2

Structural characteristics of polyaromatic compounds produced according to embodiments of the methods disclosed herein.

| Characteristics | PAC-1 | PAC-2 | PAC-3 | PAC-4 |
|---|---|---|---|---|
| $T_g$, ° C. | — | 99.7 | — | — |
| Total CO | 64 | 74 | 99 | 43 |
| Non-conjugated CO | 32 | 34 | 55 | 27 |
| Conjugated CO | 32 | 40 | 44 | 16 |
| Total COOR | 24 | 26 | 19 | 16 |
| Aliphatic COOR | 20 | 21 | 16 | 15 |
| Conjugated COOR | 4 | 5 | 3 | 1 |
| Total OH | 128 | 127 | 161 | 144 |
| Aliphatic | 36 | 35 | 65 | 56 |

TABLE 2-continued

Structural characteristics of polyaromatic compounds produced according to embodiments of the methods disclosed herein.

| Characteristics | PAC-1 | PAC-2 | PAC-3 | PAC-4 |
|---|---|---|---|---|
| Primary | 17 | 26 | 45 | 28 |
| Secondary | 19 | 9 | 20 | 28 |
| Phenolic | 92 | 92 | 96 | 88 |
| S/G ratio | 0.57 | 0.53 | 0.56 | 1.40 |
| ArH | 201 | 205 | 204 | 185 |
| Degree of condensation (DC), % | 62 | 60 | 60 | 57 |
| β-O-4 | trace | trace | trace | trace |
| β-β | trace | trace | trace | trace |
| β-5 | trace | trace | trace | trace |
| OCH$_3$ | 73 | 66 | 52 | 102 |
| Oxygenated aliphatic | 80 | 80 | 60 | 80 |
| Saturated aliphatic | 103 | 94 | 80 | 49 |
| Sugars (approximate) | 1 | 1 | 3 | 3 |
| M$_n$, Da | 1240 | 1281 | — | — |
| M$_w$, Da | 3350 | 3784 | — | — |
| Polydispersity Index (PDI) | 2.70 | 2.95 | — | — |

"—" = not measured
*units are "per 100 Ar" unless otherwise notes

Example 3

This example demonstrates one embodiment of the production and collection of polyaromatic compound. ⅜" chips produced from a mixture of lignocellulosic hardwood species were mixed with water in a 6:1 water to dry solid ratio. The mixture was heated to about 180-205° C. at a pressure sufficient to keep the fluid in liquid form (generally less than about 240 psig) and held at that temperature for about 20-35 minutes in a horizontal screw digester. Digested wood chips and liquids were separated, and the digested chips were employed in Example 4. The liquids correspond to a xylo-oligosaccharide (XOS) stream.

The XOS stream was acidified under the following conditions: 95-150° C., 0.1-6% sulfuric acid, 10-500 g/L oligomer, 5 min to 5 hours. The precipitated material (polyaromatic compound (PAC-4)) was collected by filtration, re-slurried in water to form a fine suspension, filtered, exhaustively washed on the filter with water, and dried (see Table 2).

Example 4

This example demonstrates one embodiment of the production and collection of polyaromatic compound. The digested wood chips from Example 3 were run through a steam mixing screw and horizontal screw digester at a temperature of about 190-240° C. at a pressure of less than about 500 psig for about 5-30 minutes residence time. The biomass was discharged through a blow line, causing the pressure to rapidly drop and the biomass to explode into smaller particles. These size-reduced particles were slurried with water and subjected to a temperature of about 350-400° C. for a period of less than about 10 sec under a pressure sufficient to keep the fluid in liquid or supercritical form (generally less than about 250 bar, though higher pressures typically up to about 600 bar can be employed). The resulting mixture was then subjected to solid/liquid separation. The liquid stream corresponds to a gluco-oligosaccharides (GOS) stream.

The GOS stream was acidified under the following conditions: 95-150° C., 0.1-6% sulfuric acid, 10-500 g/L oligomer, 5 min to 5 hours. The precipitated material (polyaromatic compound (PAC-3)) was cooled to about 60° C. or less while stirring, and the cooled mixture filtered through a 25 micron bag filter, with the PAC-3 material captured in the bag. PAC-3 was re-slurried in water to form a fine suspension, filtered, exhaustively washed on the filter with water, and dried (see Table 2).

Example 5

This example demonstrates the performance of an adhesive prepared using PAC-1. A commercial liquid resol-type phenol-formaldehyde (PF) resin was sourced and used in combination with PAC-1 from Example 1 at various ratios for subsequent testing using the "ABES" system (Automatic Bond Evaluation System). The ABES system is commercially available from Adhesive Evaluation Systems, Inc. The commercial resin ("PlyPF") was a somewhat condensed PF resin with a solids content of about 44% (including about 8.5% NaOH) and a viscosity of about 750 cps at 25° C., suitable for softwood plywood manufacture.

The glue was formed using PAC-1 from Example 1. PAC-1 was first ground into a fine powder and then mixed manually and thoroughly with the PlyPF resin in a specific dry weight amount (30 wt. % of the PlyPF resin substituted with PAC-1 on a dry basis), thereby forming the glue. The moisture content of a test sample was determined by the oven-drying method to be used in the calculation of the dry weight mixing amount. Sliced maple veneers 117 mm×20 mm×0.8 mm (conditioned at 50% HR & 20 C) were used for the test. The glue was applied in a way to form a bonding area of 20 mm×5 mm.

Figure 2:
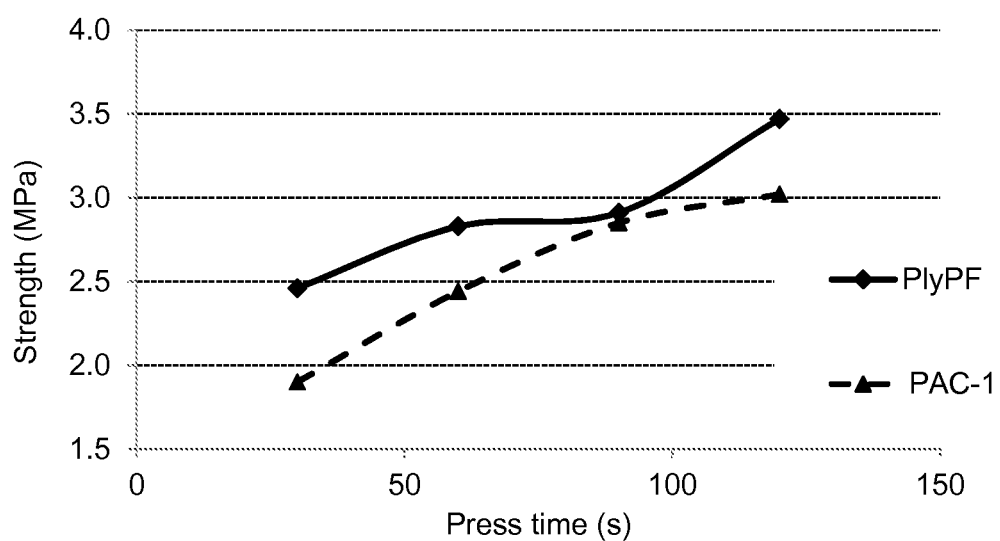
FIG. 2 illustrates the strength of an adhesive comprising a polyaromatic compound prepared according to one embodiment of the methods described herein.

Almost immediately after each bond was cured to the required level, it was tested to destruction in shear mode. Tensile load was monitored digitally during bond pulling and shear-stress-to-failure (area corrected peak load) was calculated. Five replicates were performed for each resin sample. Cure speed test was performed at 120° C. at selected press time points. The results comparing the commercial PlyPF resin with the glue comprising the PlyPF resin with 30 wt. % replaced with PAC-1 (dry basis) is shown in FIG. 2. It is significant to note that while the PlyPF resin alone appears to perform somewhat better than the mixture of PlyPF and PAC-1, the mixture nevertheless may perform adequately for certain applications. Incorporation of PAC-1 into adhesives, therefore, is attractive from an environmental standpoint (replacing petroleum-based PF resin with a sustainable material), and may also help reduce costs (PF resin is expensive).

When ranges are used herein for physical properties, such as molecular weight, or chemical properties, such as chemical formulae, all combinations, and sub-combinations of ranges specific embodiments therein are intended to be, and are, included.

The disclosures of each patent, patent application, and publication cited or described in this document are hereby incorporated herein by reference, in their entireties.

Those skilled in the art will appreciate that numerous changes and modifications can be made to the preferred embodiments of the invention and that such changes and modifications can be made without departing from the spirit of the invention.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke means plus function treatment for any limitations of any of the claims herein, except for those in which the claim expressly uses the words "means for" together with an associated function.

What is claimed is:

1. A method comprising:
a first subjecting step, wherein a first biomass is subjected to a first fluid comprising hot compressed water, thereby forming a first mixture;
   wherein the first mixture comprises a first liquid fraction comprising a first solubilized polyaromatic compound and a first solid fraction;
optionally, separating at least a portion of the first solid fraction from the first liquid fraction;
a first acidifying step, wherein the first liquid comprising the first solubilized polyaromatic compound is acidified at a temperature of at least about 90° C., thereby forming a second mixture comprising a first precipitated polyaromatic compound; and
a first collecting step, wherein at least a portion of the first precipitated polyaromatic compound is collected, thereby obtaining a first collected precipitated polyaromatic compound;
   wherein a substantial portion of the first collected precipitated polyaromatic compound is not discarded and is not combusted.

2. The method of claim 1, wherein at least a portion of the first collected precipitated polyaromatic compound is sold, bartered, traded, or any combination thereof; or
   wherein at least a portion of the first collected precipitated polyaromatic compound is incorporated into a product capable of sale, barter, trade, or any combination thereof.

3. The method of claim 1, wherein the first precipitated polyaromatic compound is selected from the group consisting of lignin, pseudolignin, a polyfuranic compound, and any combination thereof.

4. The method of claim 1, wherein the first fluid has a temperature of about 130° C. to about 374° C.

5. The method of claim 1, wherein the first fluid consists essentially of hot compressed water.

6. The method of claim 1, wherein the first liquid comprising the first solubilized polyaromatic compound does not comprise spent liquor.

7. The method of claim 1, wherein the first biomass is raw biomass.

8. The method of claim 1, wherein the first biomass is obtained by a process selected from the group consisting of acid hydrolysis, enzymatic hydrolysis, sulfur dioxide treatment, hot compressed water treatment, and any combination thereof.

9. The method of claim 1, wherein at least a portion of the first solid fraction or a first solid derived from the first solid fraction is, in a second subjecting step, subjected to a third fluid comprising hot compressed water, thereby forming a third mixture, wherein the third mixture comprises a second liquid fraction comprising a second solubilized polyaromatic compound and a second solid fraction.

10. The method of claim 9, wherein the hot compressed water in the third fluid is supercritical water.

11. The method of claim 9, wherein the third fluid consists essentially of hot compressed water.

12. The method of claim 9, wherein the second subjecting step employs the first solid derived from the first solid fraction, wherein the first solid derived from the first solid fraction is obtained by exposing the first solid fraction to a process selected from the group consisting of acid hydrolysis, enzymatic hydrolysis, sulfur dioxide treatment, hot compressed water treatment, and any combination thereof.

13. The method of claim 9, further comprising:
optionally, separating at least a portion of the second solid fraction from the second liquid fraction;
a second acidifying step, wherein the second liquid comprising the second solubilized polyaromatic compound is acidified at a temperature of at least about 90° C., thereby forming a fourth mixture comprising a second precipitated polyaromatic compound; and
a second collecting step, wherein at least a portion of the second precipitated polyaromatic compound is collected, thereby obtaining a second collected precipitated polyaromatic compound;
   wherein a substantial portion of the second collected precipitated polyaromatic compound is not discarded and is not combusted.

14. The method of claim 13, wherein at least a portion of the second collected precipitated polyaromatic compound is sold, bartered, traded, or any combination thereof; or
   wherein at least a portion of the second collected precipitated polyaromatic compound is incorporated into a product capable of sale, barter, trade, or any combination thereof.

15. The method of claim 13, wherein the second precipitated polyaromatic compound is selected from the group consisting of lignin, pseudolignin, a polyfuranic compound, and any combination thereof.

16. The method of claim 13, wherein the second liquid comprising the second solubilized polyaromatic compound does not comprise spent liquor.

17. The method of claim 2, wherein at least a portion of the first collected precipitated polyaromatic compound is incorporated into a product capable of sale, barter, trade, or any combination thereof, and the product is a thermoplastic.

18. The method of claim 2, wherein at least a portion of the first collected precipitated polyaromatic compound is incorporated into a product capable of sale, barter, trade, or any combination thereof, and the product is an adhesive.

19. The method of claim 14, wherein at least a portion of the second collected precipitated polyaromatic compound is incorporated into a product capable of sale, barter, trade, or any combination thereof, and the product is a thermoplastic.

20. The method of claim 14, wherein at least a portion of the second collected precipitated polyaromatic compound is incorporated into a product capable of sale, barter, trade, or any combination thereof, and the product is an adhesive.

* * * * *